United States Patent
Harish

(10) Patent No.: US 8,174,272 B2
(45) Date of Patent: May 8, 2012

(54) ANALYSIS OF A MATERIAL WITH CAPACITIVE TECHNOLOGY

(75) Inventor: Divyasimha Harish, Fremont, CA (US)

(73) Assignee: YPoint Capital, Inc., Fremont, CA (US)

( * ) Notice: Subject to any disclaimer, the term of this patent is extended or adjusted under 35 U.S.C. 154(b) by 657 days.

(21) Appl. No.: 12/343,227

(22) Filed: Dec. 23, 2008

(65) Prior Publication Data

US 2009/0160460 A1    Jun. 25, 2009

Related U.S. Application Data

(60) Provisional application No. 61/016,465, filed on Dec. 23, 2007.

(51) Int. Cl.
*G01R 27/26* (2006.01)
(52) U.S. Cl. .................................................. 324/674
(58) Field of Classification Search .................. 324/674
See application file for complete search history.

(56) References Cited

U.S. PATENT DOCUMENTS

| | | | |
|---|---|---|---|
| 4,785,245 A * | 11/1988 | Lew et al. | 324/308 |
| 6,426,635 B1 * | 7/2002 | Nussbaum | 324/686 |
| 6,828,800 B2 * | 12/2004 | Reich et al. | 324/658 |
| 7,126,351 B2 * | 10/2006 | Claus | 324/663 |
| 7,187,185 B2 * | 3/2007 | Dallenbach et al. | 324/662 |
| 7,205,780 B2 * | 4/2007 | Pasero et al. | 324/667 |
| 7,301,351 B2 * | 11/2007 | Deangelis et al. | 324/687 |
| 7,504,787 B2 * | 3/2009 | Hansson et al. | 318/266 |
| 2007/0108994 A1 * | 5/2007 | Chung et al. | 324/663 |

* cited by examiner

*Primary Examiner* — Jeff Natalini
(74) *Attorney, Agent, or Firm* — Rai Abhyanker

(57) ABSTRACT

Several apparatuses and a method for enabling of analysis of a material based on capacitive technology are disclosed. In an embodiment, the apparatus includes a first conductive surface. A second conductive surface is located substantially parallel to the first conductive surface. A measurement module measures a change in capacitance produced when a material is passed between the first conductive surface and the second conductive surface. The apparatus may include a database comprising a capacitance value of the material. A change in capacitance may be compared to the database to generate an identity of the material. A reference capacitor may enable the measurement module to adjust the measurement based on an environmental condition.

20 Claims, 9 Drawing Sheets

CIRCULAR COLUMN CHROMATOGRAPHY DEVICE 400

ANALYSIS OF A MATERIAL WITH CAPACITIVE TECHNOLOGY

CLAIM OF PRIORITY

This application claims priority from U.S. Provisional Patent Application No. 61/016,465 filed on Dec. 23, 2007.

FIELD OF TECHNOLOGY

This disclosure relates generally to the technical fields of measuring devices and, in one example embodiment, to a method and several apparatuses of analysis of a material with capacitive technology.

BACKGROUND

A capacitor may be a measurement tool which is often used to detect a force or pressure applied to the capacitor based on a change in distance or area between two conductor plates forming the capacitor due to the force or pressure. Since the capacitor is often sealed within a housing and/or is used to measure the force or pressure applied from outside, the capacitor is mainly used as a transducer which converts a mechanical energy (e.g., the force or pressure) to an electrical signal (e.g., capacitance, voltage, current, frequency, etc.).

On the other hand, a column chromatography device may be used to analyze a material being tested (e.g., and/or separate the material into various components). The column chromatography may be performed using either a liquid or a gas as a mobile phase. In a liquid column chromatography, a column is packed with a stationary layer. A material being analyzed may pass through the stationary layer (e.g., an octadecylsilyl) by a liquid (e.g., a water-methanol mixture pressured or forced to move). In the case of a gas column chromatography, a material being tested carried by a mobile gas (e.g., a Helium) passes through a solid stationary (e.g., a liquid silicon-based material).

During the performance of the liquid or gas column chromatography, a participant (e.g., a lab technician) often relies on his or her acumen (e.g., visual perception) in analyzing the material being tested. The process is often labor-intensive and/or error-prone. The use of complex modern equipment for the analysis may be more accurate but drive up the cost of analysis.

SUMMARY

Several apparatuses and a method for enabling of analysis of a material based on capacitive technology are disclosed.

In one aspect, the apparatus includes a first conductive surface. A second conductive surface is located substantially parallel to the first conductive surface. A measurement module measures a change in capacitance produced when a material is passed between the first conductive surface and the second conductive surface. The apparatus may include a database comprising a capacitance value of the material. A change in capacitance may be compared to the database to generate an identity of the material. A reference capacitor associated with the apparatus may enable the measurement module to adjust the measurement based on an environmental condition.

The measurement module may apply an algorithm that converts a change in capacitance to at least one of a change in voltage and a change in frequency to generate a measurement. The apparatus may further include a third conductive surface, and a fourth conductive surface substantially parallel to the third conductive surface. The apparatus may further include a measurement module to measure a change in capacitance produced when the material is passed between the third conductive surface and the fourth conductive surface after it has passed between the first surface and the second surface.

In another aspect, the apparatus includes a reference capacitor whose capacitance changes based on an environmental condition surrounding the apparatus. The apparatus includes a sensor capacitor whose capacitance changes when a material is passed through the sensor capacitor and the environmental condition, and a circuit to generate a measurement after removing an effect of the environmental condition from a capacitance of the sensor capacitor. The sensor capacitor may include at least one of a circular and a rectangular column housing with two concentric conductor plates comprising an inner conductor plate and an outer conductor plate. The material may be passed between the two concentric conductor plates. The other sensor capacitor may be formed between the inner conductor plate and the outer conductor plate. The sensor capacitor and the other sensor capacitor may be isolated by a dielectric material.

The apparatus may include a separator module that may separate the material from an other material before passing the material through the sensor capacitor. An identification module of the apparatus may identify the material based on the change of capacitance when the material is passed through the sensor capacitor and may adjust the measurement based on a value of the environmental condition communicated by the reference capacitor. An identification module of the apparatus may adjust the measurement based on a retention time of the material in the sensor capacitor.

In yet another aspect, a method includes creating an electromagnetic field between a first conductive surface and a second conductive surface substantially parallel to the first conductive surface. The material is passed through the electromagnetic field between the first conductive surface and the second conductive surface. A change in capacitance is measured between the first conductive surface and the second conductive surface. The change in capacitance may be compared with a data base including a known capacitance of the material in order to identify the material.

The method may further include comparing the change in capacitance with a data base comprising a known capacitance of the material to identify at least one of the material and a property change of the material. The method may include measuring an other change in capacitance with a reference capacitor whose capacitance changes based on an environmental condition surrounding the first conductive surface and the second conductive surface. The method may include applying an algorithm to the change in capacitance to convert the change in capacitance to a change in voltage and/or a change in frequency to generate the measurement.

The method may include transforming the measurement into a digital value and algorithmically modifying the digital value to increase the accuracy of an identification of the material. The method may also include isolating the material from an other material prior to passing the material between the first conductive surface and the second conductive surface. The method may further include adjusting the measurement based on the environmental condition. A machine may be caused to perform the method using a processor and a physical memory when a set of instructions in a form of a machine-readable medium is executed by the machine.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1A:
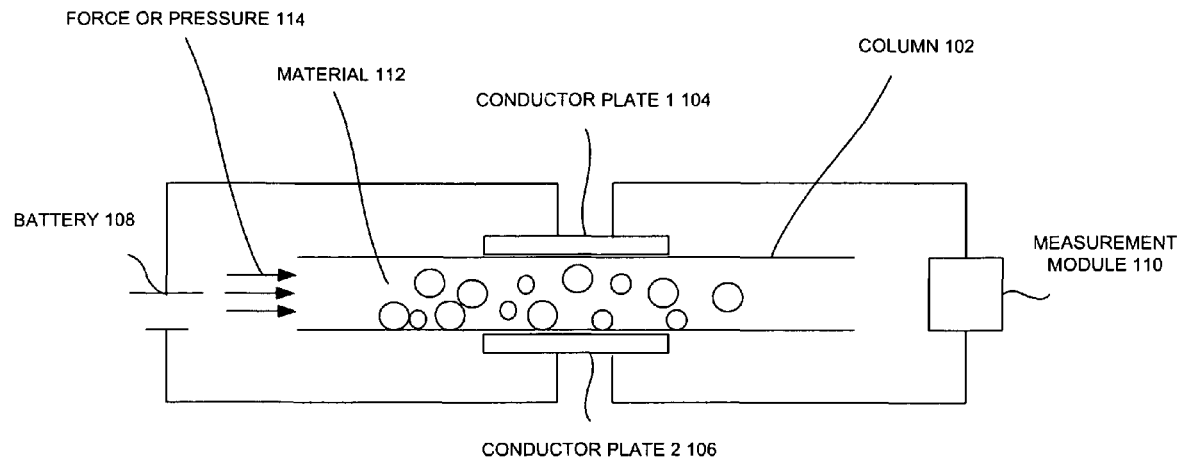
FIG. 1A is an exemplary cross-sectional view of a dielectric changing capacitive device with its conductor plates formed outside a column of the dielectric changing capacitive device, according to one embodiment of the present invention.

FIG. 1A is an exemplary cross-sectional view of a dielectric changing capacitive device with its conductor plates formed outside a column 102 of the dielectric changing capacitive device, according to one embodiment of the present invention. In FIG. 1A, a dielectric changing capacitor is formed between a conductor plate 1 104 and a conductor plate 2 106 charged by a battery 108. Because there may be no current flow once the conductor plates (e.g., made of a titanium, a gold, a nickel, a copper, an iridium, a platinum, a palladium, a carbon black, and their combinations) are fully charged, the capacitive device is more energy efficient than a measuring device based on a resistor.

The conductor plates are also connected to a measurement module (e.g., a measurement circuit based on a Wheatstone Bridge) to measure the capacitance formed between the conductor plate 1 104 and the conductor plate 2 106. In FIG. 1A, the conductor plates are formed outside the column 102 (e.g., a passageway or a channel). In one example embodiment, a material 112 may pass through the column 102 (e.g., when a force or pressure 114 is applied) and cause a change in capacitance formed between the conductor plates. In the normal mode, the column 102 may be filled with a liquid (e.g., a mineral oil, a synthetic oil, etc.) or gaseous dielectric material (e.g., an air, a nitride, a sulfur hexafluoride, etc.).

A change in capacitance may be detected when the material 112 passes through the conductor plates, thus changing the medium which is resistant to the electric field formed between the conductor plates. For example, if a dielectric material present during the normal mode of the dielectric changing capacitive device is an air (e.g., having the permittivity or dielectric constant of 1), there will be a change in capacitance between the conductor plates when blood (e.g., having the permittivity or dielectric constant of 0.8) passes through the column 102.

With the area and distance of the conductor plates being equal, the capacitance detected by the two conductor plates goes down because the permittivity of blood is less that of air (e.g., and/or because capacitance is proportional to the permittivity as illustrated in $C=kA/d$ where $C$=capacitance, $k$=permittivity, $A$=overlapping area of the conductor plates, and $d$=distance between the conductor plates). The capacitance goes down by 20%.

In one example embodiment, the dielectric changing capacitive device may be used as a tool to detect a medicine being administered to a patient in a hospital environment and/or generates an alarm when the fluid is no longer being administered. In another example embodiment, the dielectric changing capacitive device may be used as a tool to identify a material being tested based on its capacitance value.

Furthermore, the dielectric changing capacitive device may be built in a microscopic scale based on a microelectromechanical system (MEMS). A dielectric changing capacitive device based on such a fabrication process may be more sensitive to a change of the dielectric material because the area (A) and/or distance (d) of the device is miniscule. In one example embodiment, the diameter of the column 102 may be between 1 micrometer and 100 micrometers. The column 102 may be formed by an etching, photolithographic, and/or printing process. The conductor plates may be formed by a physical vapor deposition, a chemical vapor deposition, and/or an electroplating.

The measurement module 110 may be installed adjacent to the conductor plates, or they may be remotely located from the conductor plates. Additionally, the dielectric changing capacitive device may require a low voltage (e.g., ranging from 1 millivolt to 1 volt) to operate than a sensor or detector of larger scale. In another example embodiment, the measurement module 110 may be equipped with a database of capacitance values associated with various materials. Then, the capacitance of a tested material may be compared against the database to promptly generate the identity of the tested material.

Figure 1B:
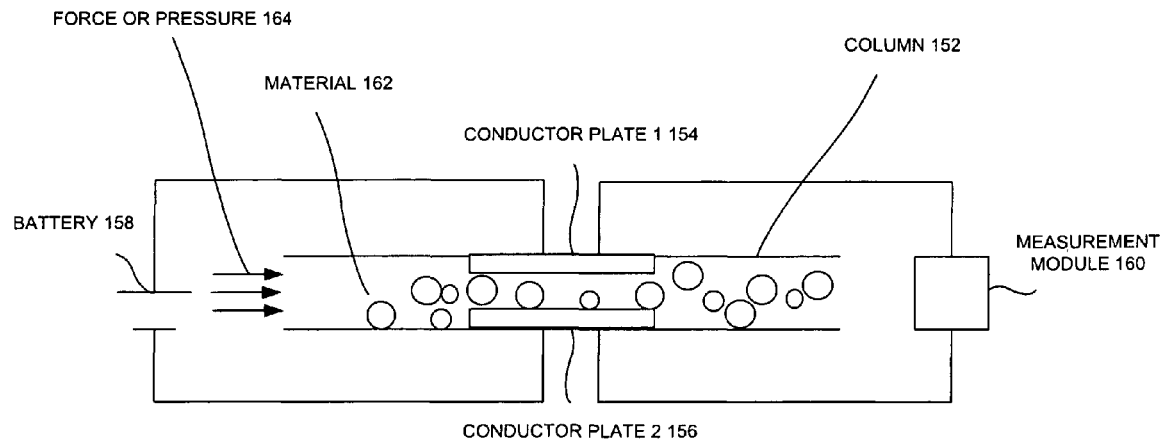
FIG. 1B is an exemplary cross-sectional view of a dielectric changing capacitive device with its conductor plates formed inside the column of the dielectric changing capacitive device, according to one embodiment of the present invention.

FIG. 1B is an exemplary cross-sectional view of a dielectric changing capacitive device with its conductor plates formed inside the column of the dielectric changing capacitive device, according to one embodiment of the present invention. The dielectric changing capacitive device of FIG. 1B may operate similar to that of FIG. 1A. As illustrated in FIG. 1B, a conductor plate 1 154 and a conductor plate 2 156 are fabricated inside a column 152 rather than outside.

Figure 2:
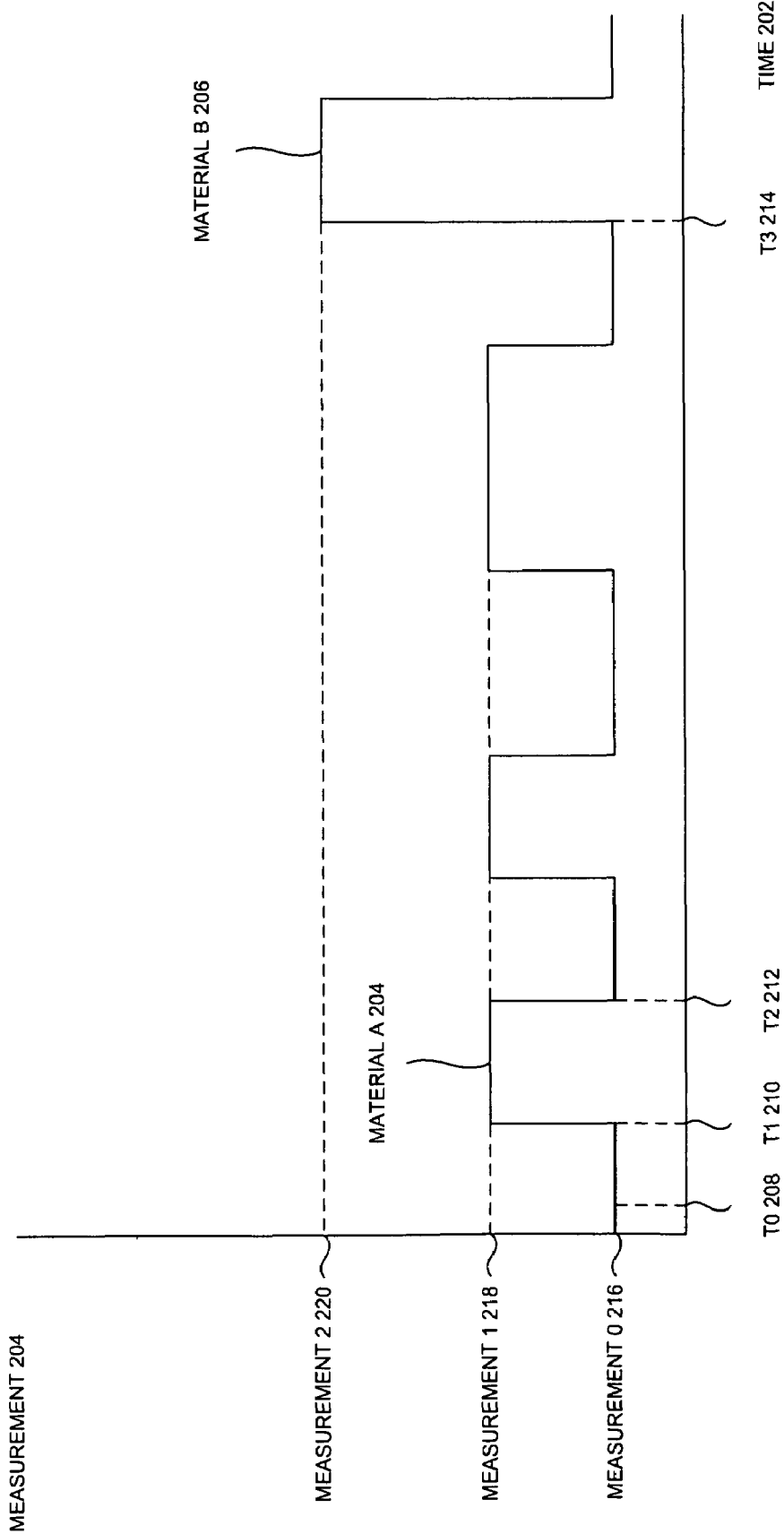
FIG. 2 is an exemplary graph of materials detected by the dielectric changing capacitive device of FIG. 1A or FIG. 1B, according to one embodiment of the present invention.

FIG. 2 is an exemplary graph of materials detected by the dielectric changing capacitive device of FIG. 1A or FIG. 1B, according to one embodiment of the present invention. As illustrated in FIG. 2, the dielectric changing capacitive device is in a normal mode at T0 208 with the gap between the conductor plates is filled with a default dielectric medium (e.g., such as an air, an ammonium gas, etc.). At T1 210, the measurement value (e.g., a voltage, a current, a capacitance, a frequency, etc.) increases from a measurement 0 216 to a measurement 1 218 as a material A 204 passes between the two conductor plates. Once the flow of the material A 204 is completed at T2 212, the measurement value returns to its normal value of the measurement 0 216.

At T3 214, the measurement value increases to the measurement 2 220 as a material B 206 passes between the two conductor plates. The graph illustrates that the permittivity (e.g., which is a physical quantity that describes how an electric field affects and is affected by a dielectric medium, and is determined by the ability of a material to reduce the total electric field inside the material) of the material B 206 is larger than the permittivity of the material A 204 and/or the permittivity of the material A 204 is larger than the permittivity of the dielectric material present between the two conductor plates during the normal mode.

Figure 3:
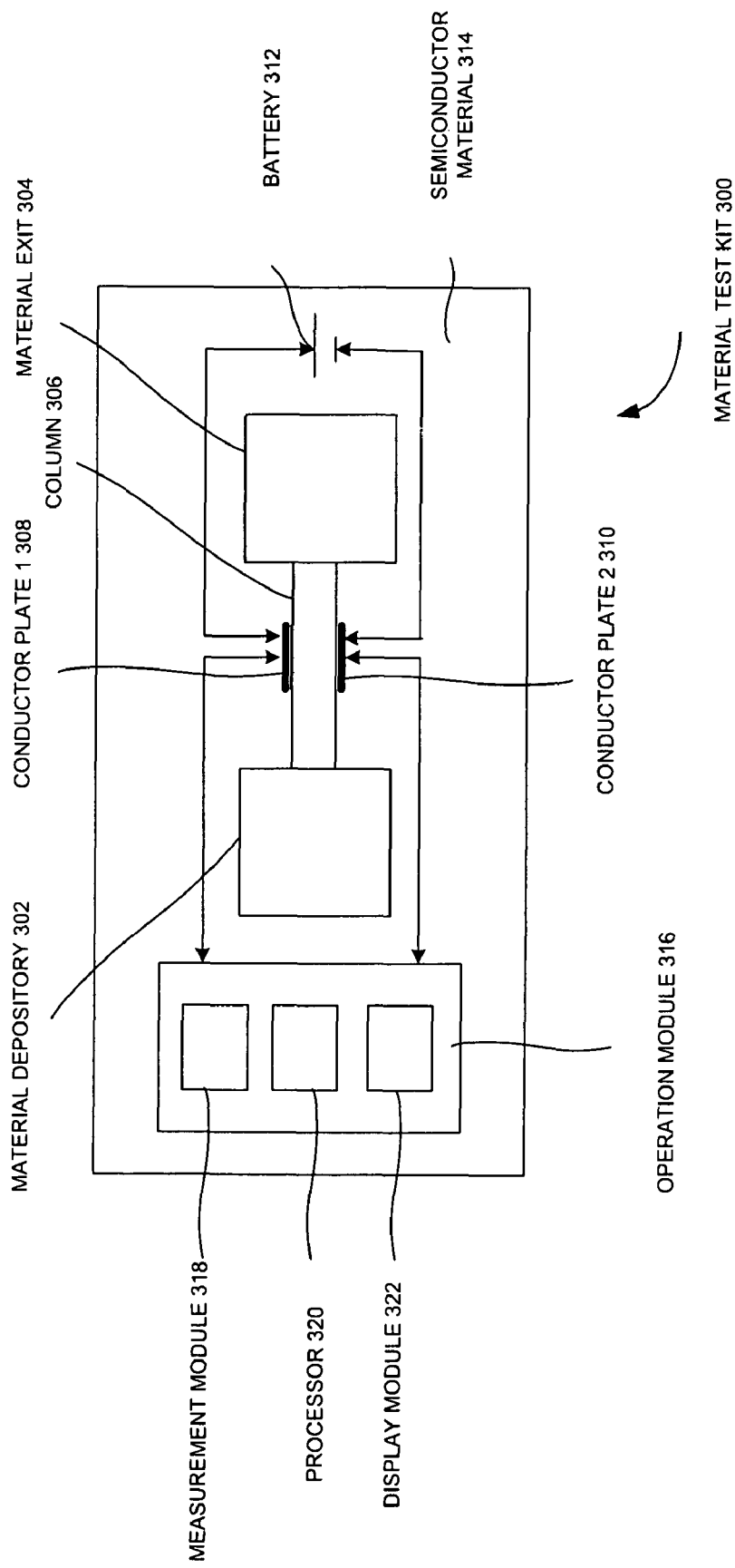
FIG. 3 is an exemplary schematic diagram of a material testing kit based on a dielectric changing capacitive device, according to one embodiment of the present invention.

FIG. 3 is an exemplary schematic diagram of a material test kit 300 based on the dielectric changing capacitive device, according to one embodiment of the present invention. In FIG. 3, a material to be tested may be deposited to a material depository 302. When a force or pressure is applied towards the material depository 302, the material may flow through a capacitor formed by a conductor plate 308 and a conductor plate 2 310. The material may exit through a material exit 304 formed opposite to the material depository 302.

Like the dielectric changing capacitive device of FIGS. 1A and 1B, the conductor plates of the material test kit 300 is powered by a battery 312. In one example embodiment, the capacitor may be formed on a semiconductor material 314 (e.g., a glass, a silicon, a plastic, a composite material, etc.). In another example embodiment, an operation module 316 of the material test kit 300 may include a measurement module 318, a processor 320, and/or a display module 322. The measurement module 318 may be used to measure the capacitance formed between the conductor plates.

The processor 320 (e.g., a microcontroller) may be used to process the measurement obtained from the measurement module 318 based on a set of instructions (e.g., preprogrammed) embedded in the processor 320. For instance, the measurement may be converted to various measurement units (e.g., in frequency, voltage, current, etc.). Additionally, the measurement may be converted to a digital value for a later processing and/or to increase its accuracy.

The display module 322 (e.g., a LED, a LCD, a litmus paper, etc.) may be used to inform the result of the analysis performed on the material. For example, the material test kit 300 may be specifically geared towards the analysis of a particular type of material (e.g., such as a urine analysis, a toxicity analysis, a blood sugar level analysis, etc.). In one example embodiment, the material test kit 300 may have multiple columns and/or multiple capacitors to analyze different components present in a test material based on a column chromatography (e.g., as will be illustrated in details in FIGS. 4, 5, 6, and 7).

Figure 4:
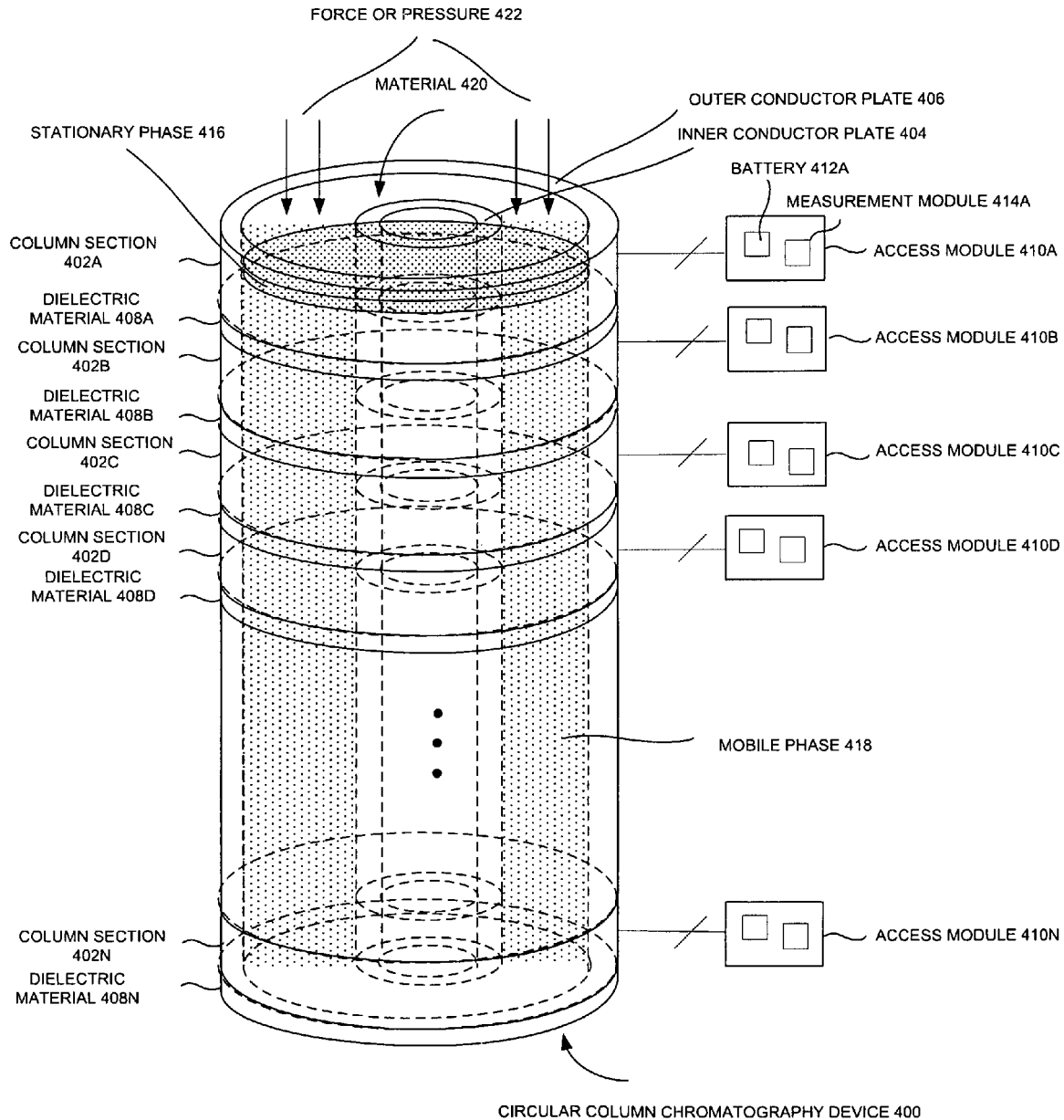
FIG. 4 is an exemplary three-dimensional view of a circular column chromatography device based on dielectric changing capacitive technology, according to one embodiment of the present invention.

FIG. 4 is an exemplary three-dimensional view of a circular column chromatography device 400 based on dielectric changing capacitive technology, according to one embodiment of the present invention. In FIG. 4, the circular column chromatography device 400 includes two concentric conductor plates (e.g., an inner conductor plate 404 and an outer conductor plate 406). One or multiple capacitors may be formed between the inner conductor plate 404 and the outer conductor plate 406. To timely detect various component of a material (e.g., or a mixture) being tested, the circular column chromatography device 400 may be divided into multiple sections (e.g., a column section 402A, a column section 402B, a column section 402C, a column section 402D, and/or a column section 402N).

The column sections may be isolated from each other using the dielectric materials (e.g., a dielectric material 408A, a dielectric material 408B, a dielectric material 408C, a dielectric material 408D, and/or a dielectric material 408E). For example, the dielectric material 408A (e.g., a ceramic, a plastic, a wood, etc.) may be used to separate the capacitor of the column section 402A from the capacitor of the column section 402B.

Each column section is connected to an access module (e.g., an access module 410A, an access module 410B, an access module 410C, an access module 410D, and an access module 410N). The access module includes a battery (e.g., a battery 412A, a battery 412B, a battery 412C, a battery 412D, and/or a battery 412N) and a measurement module (e.g., a measurement module 414A, a measurement module 414B, a measurement module 414C, a measurement module 414D, and/or a measurement module 414N).

In addition, a stationary phase 416 or an immobilized phase is formed toward the top of the circular column chromatography device 400. In one example embodiment, the stationary phase 416 may formed by packing the upper part of column with irregularly or spherically shaped particles or porous monolithic layer (e.g., a silica, an octadecylsily, etc.) when a mobile phase 418 (e.g., a water-methanol mixture, a toluene, etc.) or an eluent is a liquid. In another example embodiment, the stationary phase 416 may be packed with a liquid silicon-material when the mobile phase 416 is a gas (e.g., a Helium).

In yet another example embodiment, a material 420 or an analyte (e.g., a protein, a synthetic material, and/or other chemical or biological compound) may be forced or pressured through the stationary phase 416 (e.g., using a force or pressure 422) and carried by the mobile phase 418. The process performed by the circular column chromatography device 400 may involve separating mixtures and identifying components of the material 420 (e.g., a sample).

The process exploits the differences in partitioning behavior of analytes between the mobile phase 418 and the stationary phase 416. The components of the material 420 may interact with the stationary phase 416 based on charge (e.g., ion-ion-interactions, ion-dipole-interactions, etc.), Van der Waals' forces, and/or relative solubility or adsorption (hydrophobic interactions, specific affinity).

The material 420 may be analyzed based on its retention time (e.g., which is a measure of the speed at which the material 420 moves in the circular column chromatography device 400). The retention time of the material 420 may differ considerably between experiments due to variations of the eluent, the stationary phase, temperature, sample matrix and the setup. Thus, the retention time of the material 420 may be compared to that of several standard compounds under absolutely identical conditions.

Moreover, selecting the stationary phase 416, mobile phase 418, the velocity of the material 420, the length of the column, and/or the temperature may be important in the outcome. In addition to the retention time, the measurement (e.g., in capacitance, voltage, current, frequency, etc.) detected by the access module associated each column section may be used to analyze the material 420 as well. Thus, the retention times (e.g., which may be the time between the injection time and the measurement time) and/or measurement values obtained for components making up the material 420 may be used to analyze the material 420 along with other environmental and/or experimental factors (e.g., the temperature, the velocity of the material 420, the column length, etc.).

In one example embodiment, the various measurements (e.g., taken by some or all of the column sections) and retention times of components may be compared with a set of known samples (e.g., which may be stored as a database). When a match is found, the identity of the material 420 may be generated (e.g., and/or displayed).

Figure 5:
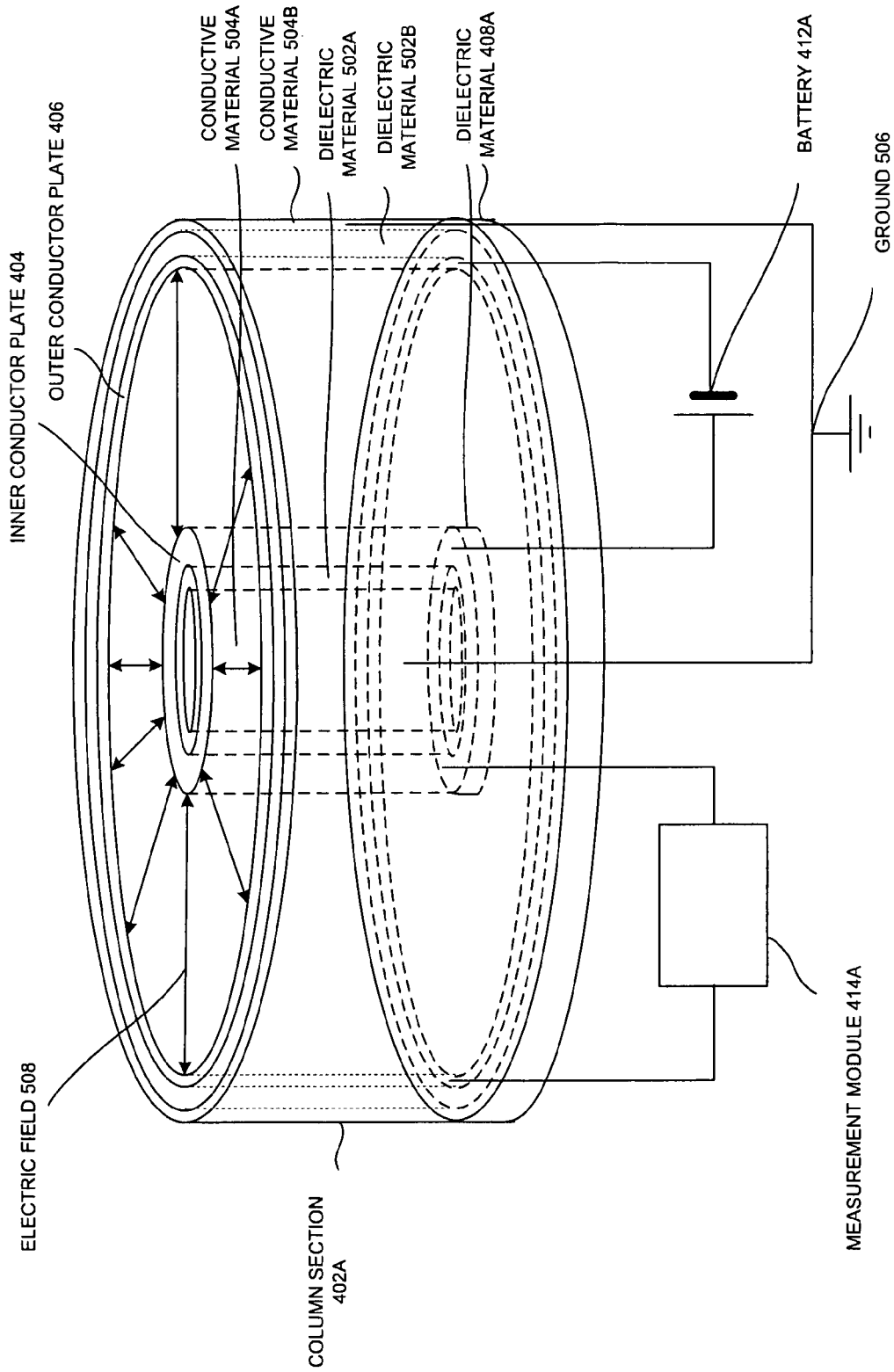
FIG. 5 is an exemplary three-dimensional view of a section of the circular column chromatography device of FIG. 4, according to one embodiment of the present invention.

FIG. 5 is an exemplary three-dimensional view of a section of the circular column chromatography device 400 of FIG. 4, according to one embodiment of the present invention. As illustrated in FIG. 5, the two conductor plates are shielded by a conductive material (e.g., a conductive material 504A and a conductive 504B) which is grounded (e.g., by connecting them to a ground 506). This way, an electric field 508 formed between the inner conductor plate 404 and the outer conductor plate 406 may be contained between the two conductor plates (e.g., thus minimizing a stray capacitance).

To supply a uniform voltage or current, the battery 412A is connected to the inner conductor plate 404 and the outer conductor plate 406. The measurement module 414A may be used to measure the material 420 or sample passing through the column section 402A. The size (e.g., a height, radius, length, etc.) of the column section 402A may be configured for the measurement of specific type of sample (e.g., or the material 420) being tested.

Figure 6:
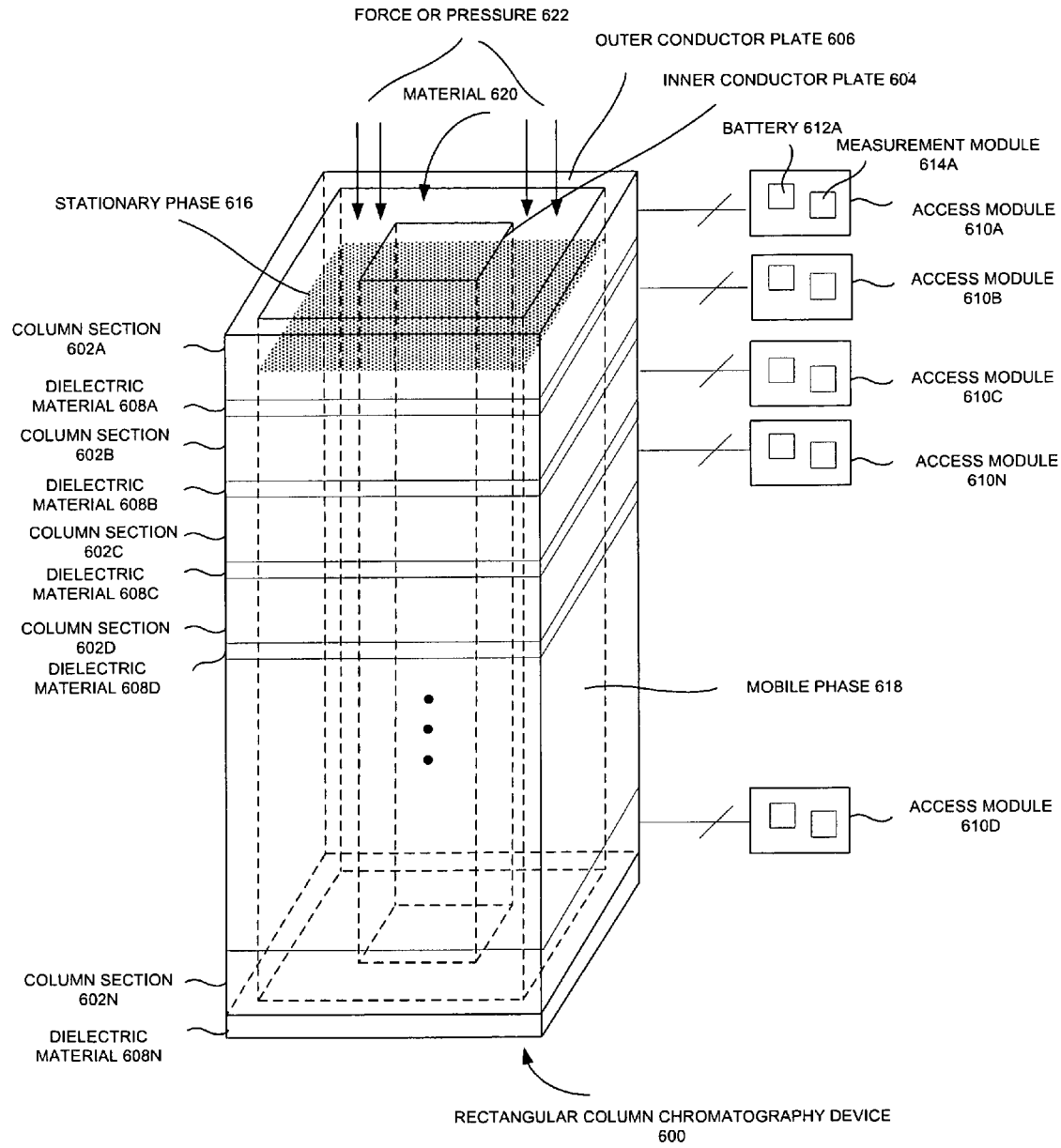
FIG. 6 is an exemplary three-dimensional view of a rectangular column chromatography device based on the dielectric changing capacitive technology, according to one embodiment of the present invention.

FIG. 6 is an exemplary three-dimensional view of a rectangular column chromatography device 600 based on dielectric changing capacitive technology, according to one embodiment of the present invention. The rectangular column chromatography device 600 may work similar to the circular column chromatography device 400 of FIG. 4 in principle. As in FIGS. 4 and 6, a column chromatography device with one or more of dielectric changing capacitive devices may take various shapes (e.g., a triangle, a pentagon, a hexagon, an octagon, etc.).

Figure 7:
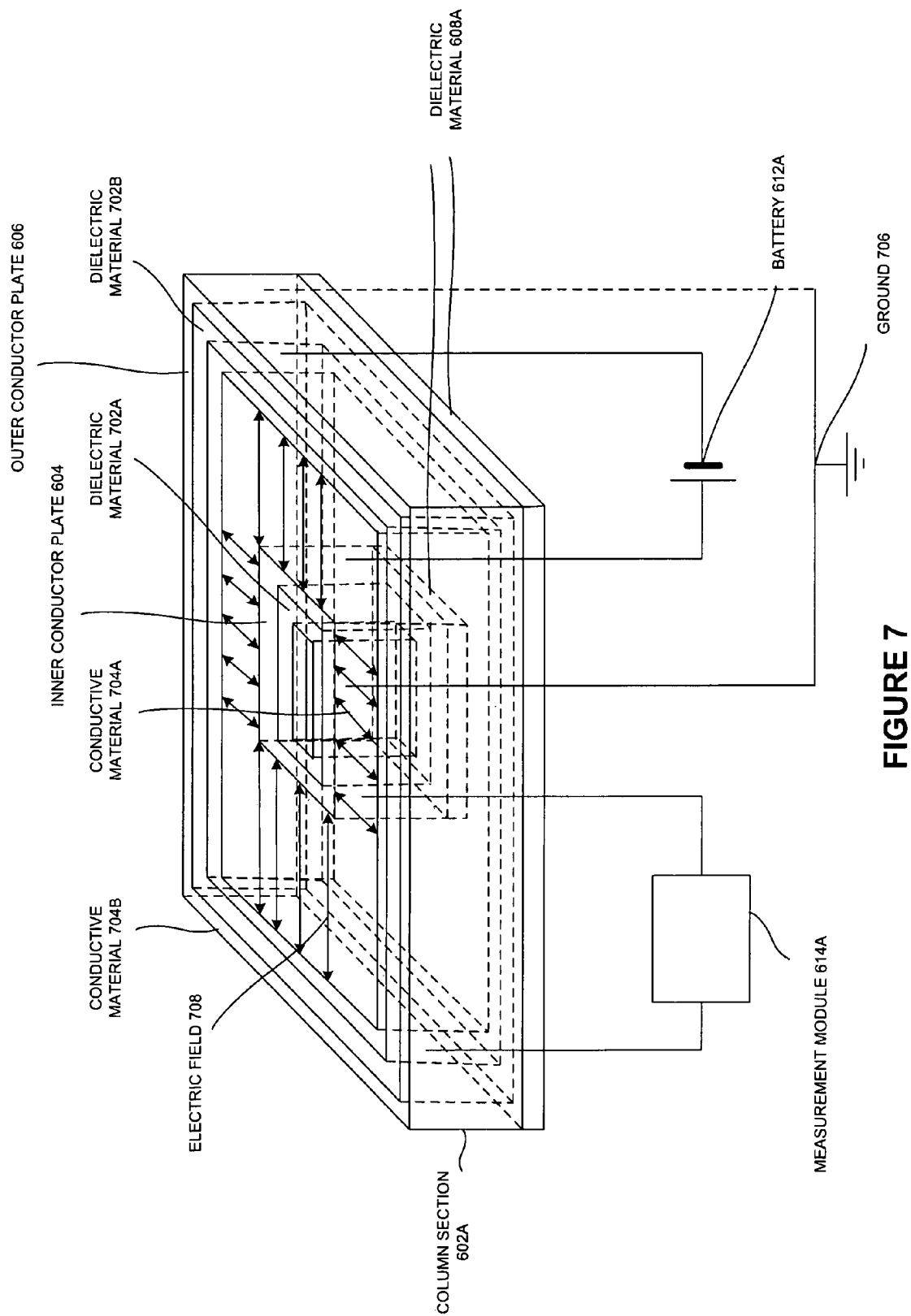
FIG. 7 is an exemplary three-dimensional view of a section of the rectangular column chromatography device of FIG. 6, according to one embodiment of the present invention.

FIG. 7 is an exemplary three-dimensional view of a section of the rectangular column chromatography device 600 of FIG. 6, according to one embodiment of the present invention. Each column section (e.g., the column section 602A) of the rectangular column chromatography device 600 may work similar to the column section (e.g., the column section 402A) of circular column chromatography device 400 of FIG. 4 in principle.

Figure 8:
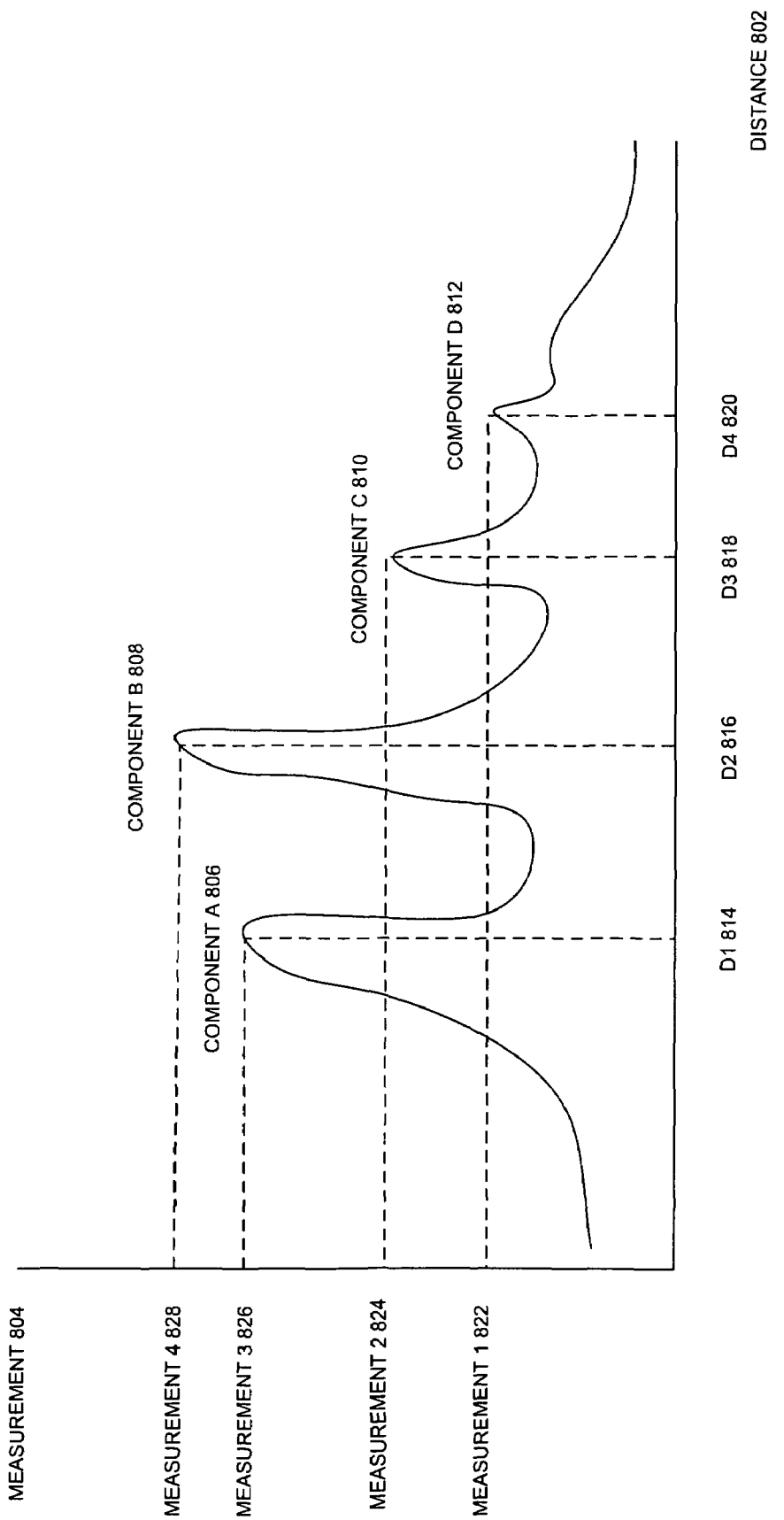
FIG. 8 is an exemplary graph of materials detected by the circular or rectangular column chromatography device of FIG. 6 or FIG. 7, according to one embodiment of the present invention.

FIG. 8 is an exemplary graph of materials detected by the circular or rectangular column chromatography device of FIG. 6 or FIG. 7, according to one embodiment of the present invention. In FIG. 8, four different components (e.g., a component A 806, a component B, 808, a component C 810, and a component D 812) of a material (e.g., an analyte) may be separated by a column chromatography device (e.g., the circular column chromatography device of FIG. 4 or the rectangular column chromatography device of FIG. 6) and analyzed based on a distance (e.g., a distance 802) each component traveled and/or its measurement (e.g., a measurement 804). Additionally, a retention time from the inception of the material to the column chromatography device to the measurement time may be obtained for further analysis.

As illustrated in FIG. 8, four distinct peaks in the graph may indicate that there are at least four components in the material being tested. In one example embodiment, FIG. 8 illustrates the measurements taken at the same time. In such a situation, the component A 806, the component B 808, the component C 810, and/or the component D 812 may travel at different speeds, thus resulting in the differences in the distances they traveled. Additionally, one or more capacitors of the column chromatography device may measure the capacitance (e.g., and/or voltage, current, frequency, etc.) of each component. Each of the components may give out a unique measurement value because it may have a unique permittivity or dielectric constant.

For example, in FIG. 8, the component A 806 travels by D1 814 while generating the measurement 3 826. The component B 808 travels by D2 816 while generating the measurement 4 828. The component C 810 travels by D3 818 while generating the measurement 2 824, and the component D 812 travels by D4 820 while generating the measurement 1 822. In another example embodiment, the measurements may be taken at different times by one or more capacitors of the column chromatography device. In yet another example embodiment, the measurements, travel distances, and/or travel times taken during a column chromatography session may be matched with a database (e.g., storing previously analyzed materials) to analyze the material. In this case, other environmental and/or experimental factors (e.g., the temperature, the velocity of the material 420, the column length, etc.) may be considered in the analysis of the material.

Figure 9:
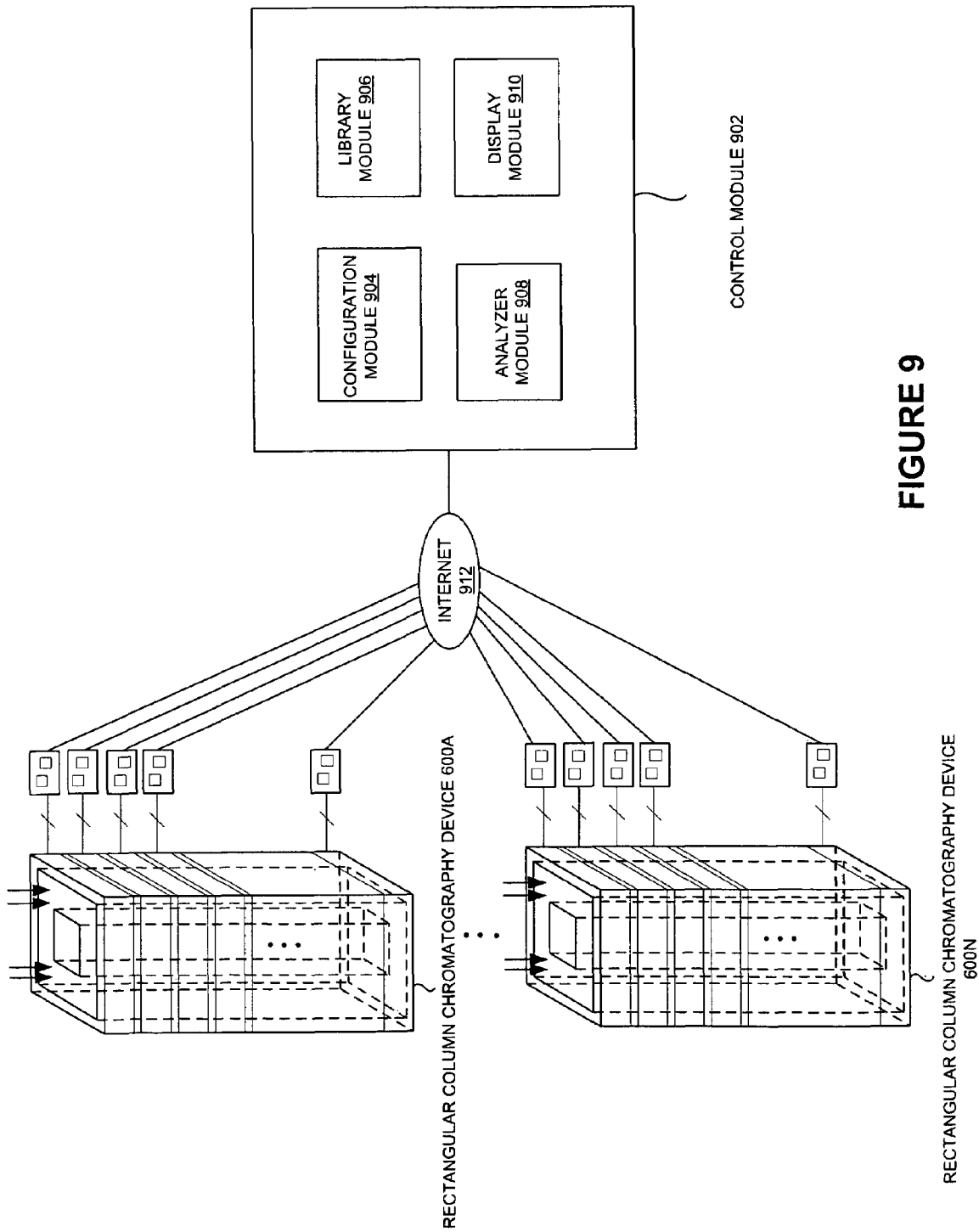
FIG. 9 is an exemplary system diagram of multiple column chromatography devices interacting with a control module, according to one embodiment of the present invention.

FIG. 9 is an exemplary system diagram of multiple column chromatography devices interacting with a control module, according to one embodiment of the present invention. In FIG. 9, one or more column chromatography devices (e.g., a rectangular column chromatography device 600A, a rectangular column chromatography device 600N) are connected to the control module 902 (e.g., remotely located) through the Internet. For example, the devices may be located in multiple locations (e.g., laboratories), and the measurements taken by each device may be reported to the control module 902 (e.g., which may be located to a supervisor's office). Alternatively, the devices and the control module 902 may be located at the same location.

The control module 902 includes a configuration module 904, a library module 906, an analyzer module 908, and a display module 910. The configuration module 904 may be used to set the devices. In one example embodiment, the configuration module 904 may be used to turn on or turn off one or more of the column chromatography devices connected to the control module 902. Additionally, the configuration module 904 may be used to individually turn on or turn off one or more access modules (e.g., the access module 602A of FIG. 6).

The library module 906 may include data of various materials which have been previously tested by similar column chromatography devices (e.g., where the data may be used to analyze a material or sample being tested by any one of the devices in FIG. 9). The library module 906 may also update the data as more samples are being tested by the devices. The analyzer module 908 may be used to determine the makeup of the material or sample being tested. The analyzer module 908 may be programmed based on the specification of a user, and may be linked with the library module 906 to perform the analysis. The display module 910 (e.g., a screen, a printout, etc.) is used to present the result of the material analysis.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The invention claimed is:

1. An apparatus, comprising:
   a first conductive surface;
   a second conductive surface substantially parallel to the first conductive surface, the second conductive surface and the first conductive surface being concentric, a column along an axis of concentricity of the first conductive surface and the second conductive surface being divided into a plurality of column sections, each of which is configured to form a capacitor based on a separation between a corresponding portion of the first conductive surface and a corresponding portion of the second conductive surface; and
   a measurement module, associated with each capacitor of the plurality of column sections and configured to measure a change in capacitance of the each capacitor produced when a material is passed between the corresponding portion of the first conductive surface and the corresponding portion of the second conductive surface.

2. The apparatus of claim 1, further comprising a database including a capacitance value of the material.

3. The apparatus of claim 2, wherein the change in capacitance is compared to the database to generate an identity of the material.

4. The apparatus of claim 1, further comprising a stationary phase to at least one of force and pressurize the material to be carried between the corresponding portion of the first conductive surface and the corresponding portion of the second conductive surface.

5. The apparatus of claim 1, wherein the measurement module is configured to apply an algorithm that converts the change in capacitance to at least one of a change in voltage and a change in frequency to generate a measurement.

6. The apparatus of claim 1, further comprising:
   a dielectric material separating a column section from an adjacent column section of the plurality of column sections.

7. An apparatus, comprising:
   a first conductive surface;
   a second conductive surface substantially parallel to the first conductive surface, the second conductive surface and the first conductive surface being concentric, a column along an axis of concentricity of the first conductive surface and the second conductive surface being divided into a plurality of column sections, each of which is configured to form a capacitor based on a separation between a corresponding portion of the first conductive surface and a corresponding portion of the second conductive surface;
   a stationary phase to at least one of force and pressurize a material to be carried between the corresponding portion of the first conductive surface and the corresponding portion of the second conductive surface; and
   an access module, associated with each capacitor of the plurality of column sections and including a battery and a measurement module, the measurement module being configured to measure a change in capacitance of the each capacitor produced when the material is passed between the corresponding portion of the first conductive surface and the corresponding portion of the second conductive surface.

8. The apparatus of claim 7, further comprising:
   a dielectric material separating a column section from an adjacent column section of the plurality of column sections.

9. The apparatus of claim 7, further comprising:
   a database including a capacitance value of the material.

10. The apparatus of claim 9,
    wherein the change in capacitance is compared to the database to generate an identity of the material.

11. The apparatus of claim 7, wherein the material is separated from another material before being passed between the corresponding portion of the first conductive surface and the corresponding portion of the second conductive surface.

12. The apparatus of claim 7, wherein the capacitance measurement is adjusted based on a retention time of the material in the each capacitor.

13. A method of a capacitive sensor comprising:
    concentrically forming a second conductive surface substantially parallel to a first conductive surface;
    dividing a column along an axis of concentricity of the first conductive surface and the second conductive surface into a plurality of column sections;
    forming, at each of the column section, a capacitor based on a separation between a corresponding portion of the first conductive surface and a corresponding portion of the second conductive surface;
    creating an electromagnetic field between the first conductive surface and the second conductive surface;
    passing a material through the electromagnetic field between the corresponding portion of the first conductive surface and the corresponding portion of the second conductive surface; and
    measuring a change in capacitance of the capacitor between the corresponding portion of the first conductive surface and the corresponding portion of the second conductive surface.

14. The method of claim 13, further comprising:
    comparing the change in capacitance with a database including a known capacitance of the material to identify at least one of the material and a property change of the material.

15. The method of claim 13, further comprising:
    separating a column section from an adjacent column section of the plurality of column sections with a dielectric material.

16. The method of claim 13, further comprising:
    applying an algorithm to the change in capacitance to convert the change in capacitance to at least one of a change in voltage and a change in frequency to generate the measurement.

17. The method of claim 16, further comprising:
    transforming the measurement into a digital value and algorithmically modifying the digital value to increase the accuracy of identification of the material.

18. The method of claim 13, further comprising:
    isolating the material from another material prior to passing the material between the corresponding portion of the first conductive surface and the corresponding portion of the second conductive surface.

19. The method of claim 13, further comprising:
adjusting the measurement based on an environmental condition.

20. The method of claim 13, further comprising at least one of forcing and pressurizing the material to be carried between the corresponding portion of the first conductive surface and the corresponding portion of the second conductive surface through a stationary phase.

* * * * *